United States Patent [19]
Weisman et al.

[11] Patent Number: 6,099,851
[45] Date of Patent: Aug. 8, 2000

[54] THERAPEUTIC USES OF LEUPROLIDE ACETATE

[76] Inventors: Kenneth M. Weisman, 30 Springton Pointe Dr., Newtown Square, Pa. 19073; Michael Goldberg, 20 Aspen Dr., Ivyland, Pa. 18974

[21] Appl. No.: 09/089,184

[22] Filed: Jun. 2, 1998

Related U.S. Application Data

[60] Provisional application No. 60/049,162, Jun. 9, 1997.

[51] Int. Cl.$^7$ .................................. A61P 9/10; A61K 9/08
[52] U.S. Cl. .......................... 424/423; 424/433; 424/449; 424/464; 514/824
[58] Field of Search ..................................... 424/464, 449, 424/423, 433; 514/824

[56] References Cited

U.S. PATENT DOCUMENTS 4,897,256   1/1990   Adjgi et al. .

*Primary Examiner*—Edward J. Webman
*Attorney, Agent, or Firm*—Caesar, Rivise, Bernstein, Cohen & Pokotilow, Ltd.

[57] ABSTRACT

A method of decreasing atherosclerosis and its complications including but not limited to myocardial infarction, stroke and peripheral vascular disease comprising administering to a human or animal an amount of Leuprolide acetate is sufficient to decrease atherosclerosis and its complications.

6 Claims, No Drawings

THERAPEUTIC USES OF LEUPROLIDE ACETATE

This application claims the benefit of the filing date of Jun. 9, 1997 of Provisional patent application serial No. 60/049,162.

BACKGROUND OF THE INVENTION

Leuprolide acetate is a synthetic nonapeptide of naturally occurring gonadotropin-releasing hormone (GnRH or LH-RH), the chemical name is 5-oxo-L-prolyl-L-histidyl-L-tryptophyl-L-seryl-L-tyrosyl-D-leucyl-L-leucyl-L-arginyl-N-ethyl-L-prolinamide acetate salt sold under the trade name Lupron or Lupron Depot, as identified by U.S. Pat. No. 4,897,256, the entire disclosure in incorporated by reference herein, is known for use in the treatment of prostatic carcinoma. Leuprolide is known to decrease levels of LHRH, LH and Testosterone (a sex hormone). This process of changing the sex hormone levels is known as hormonal manipulation.

The present invention involves the use of Leuprolide acetate in the prevention and treatment of atherosclerosis, coronary heart disease, stroke, and peripheral vascular disease.

A retrospective study was performed which compared the rates of patient reported heart attack in several groups 1—control group of males entering the urology office for any routine complaint. 2—a group of prostate cancer patients treated with Leuprolide acetate, a LHRH inhibitor. 3—a group of prostate cancer patients treated with Goserelin acetate (Zoladex), a LHRH inhibitor. 4—a group of prostate cancer patients not treated with hormonal manipulation (neither Leuprolide or Goserelin). 5—all patients on LHRH inhibitors (group 2+group 3).

The patients on either Leuprolide or Goserelin were treated with the recommended doses indicated for the treatment of prostatic carcinoma, at either one or three month intervals depending on the preparation used. Leuprolide was dosed at 7.5 mg monthly (single intramuscular injection) or at 22.5 mg at 3 month intervals (single intramuscular injection). Goserelin was dosed at 3.6 mg monthly or at a dose of 10.8 mg at 3 month intervals (subcutaneous injection).

The various groups of office patients were given a questionnaire. In groups 2 and 3 only those on drug for at least one year were considered. Cardiac event is defined either the history of a heart attack or occurrence of coronary artery bypass or angioplasty. In control groups only events occurring in the 3 years prior to the questionnaire are charted. The results were as follows:

|  | No Patients | Cardiac Events | Subject Years | Events/Year |
|---|---|---|---|---|
| Group 1 (control no cancer) | 247 | 26 | 741 | .0351 |
| Group 4 (control cancer patients) | 69 | 6 | 207 | .0290 |
| Total Control (Groups 1 + 4) | 316 | 32 | 948 | .0338 |
| Group 2 (Lupron) | 28 | 1 | 118 | .00847 |
| Group 3 (Zoladex) | 25 | 1 | 62 | .0161 |
| Group 6 (antiLHRH) groups 2 + 3 | 50 | 2 | 180 | .0111 |

The observed difference between the proportions of Total Control vs Group 6 (LHRH) is 0.0226. 95% Confidence Interval for the difference between the proportions is 0.00350 to 0.0418. Patients treated with LHRH inhibitors had fewer heart attacks than controls.

The observed difference between the proportions of Group 2 (Lupron) and Total Control is 0.253. 95% Confidence Interval for the difference between the proportions is 0.00514 and 0.0454. Patients treated with Leuprolide acetate had fewer heart attacks than controls.

In the practice of the invention the leuprolide acetate is administered as a tablet, or as a part of a liquid solution or dispersion, or patch or subcutaneous pellet in order to achieve systemic absorption of the drug.

The observed difference between the proportions of Group 3 and Total Control is 0.0177. Patients treated with Goserelin (Zoladex) had fewer heart attacks than controls.

Without further elaboration the foregoing will so fully illustrate our invention that others, may, by applying current future knowledge, adopt the same for use under various conditions of service.

What is claimed is:

1. A method of decreasing atherosclerosis and its complications, said method comprising administering to a human or animal an amount of Leuprolide Acetate sufficient to decrease atherosclerosis and its complications.

2. The method in claim 1 wherein the effective amount of Leuprolide Acetate is a 7.5 mg intramuscular injection administered monthly.

3. The invention in claim 1 wherein Leuprolide Acetate is administered as a tablet, or as a part of a liquid solution or dispersion, or patch, or subcutaneous pellet in order to achieve systemic absorption of Leuprolide Acetate.

4. The method of claim 1 wherein the method of decreasing atherosclerosis and its complications involves myocardial infarction.

5. The method of claim 1 wherein the method of decreasing atherosclerosis and its complications involves stroke.

6. The method of claim 1 wherein the method of decreasing atherosclerosis and its complications involves peripheral vascular disease.

* * * * *